(12) United States Patent
Bauer et al.

(10) Patent No.: US 7,271,113 B2
(45) Date of Patent: Sep. 18, 2007

(54) COMPOSITE WITH AN ABSORBENT LAYER

(75) Inventors: Joachim Bauer, Eggenwil (CH); Indra Roy, Eggenwil (CH)

(73) Assignee: Fiberweb Corovin GmbH (DE)

( * ) Notice: Subject to any disclaimer, the term of this patent is extended or adjusted under 35 U.S.C. 154(b) by 0 days.

(21) Appl. No.: 10/501,601

(22) PCT Filed: Jan. 23, 2003

(86) PCT No.: PCT/EP03/00635

§ 371 (c)(1),
(2), (4) Date: Jan. 27, 2005

(87) PCT Pub. No.: WO03/068121

PCT Pub. Date: Aug. 21, 2003

(65) Prior Publication Data

US 2005/0118387 A1  Jun. 2, 2005

(30) Foreign Application Priority Data

Feb. 13, 2002 (DE) .................................. 102 05 828

(51) Int. Cl.
*B32B 5/26* (2006.01)
*D04H 1/00* (2006.01)

(52) U.S. Cl. ...................... 442/381; 442/361; 442/389; 442/393

(58) Field of Classification Search ............. 428/304.4, 428/311.1, 311.7, 373, 374; 604/289, 290; 442/449, 443, 361, 381, 389, 393; 156/83
See application file for complete search history.

(56) References Cited

U.S. PATENT DOCUMENTS

| | | | | |
|---|---|---|---|---|
| 4,142,017 A | * | 2/1979 | Blackburn et al. | 442/333 |
| 4,766,029 A | * | 8/1988 | Brock et al. | 442/382 |
| 5,486,166 A | * | 1/1996 | Bishop et al. | 604/366 |
| 5,522,810 A | * | 6/1996 | Allen et al. | 604/366 |
| 5,821,179 A | * | 10/1998 | Masaki et al. | 442/375 |
| 6,559,081 B1 | * | 5/2003 | Erspamer et al. | 442/392 |
| 6,617,490 B1 | * | 9/2003 | Chen et al. | 604/380 |
| 6,787,245 B1 | * | 9/2004 | Hayes | 428/480 |
| 6,863,960 B2 | * | 3/2005 | Curro et al. | 428/198 |
| 7,176,149 B2 | * | 2/2007 | Dutkiewicz et al. | 442/375 |

FOREIGN PATENT DOCUMENTS

| | | |
|---|---|---|
| EP | 0 621 082 A | 10/1994 |
| EP | 0 845 455 A1 | 6/1998 |
| GB | 2 279 673 A | 1/1995 |
| JP | 06-134910 | 5/1994 |
| WO | WO93/20950 | 10/1993 |
| WO | WO95/03019 | 2/1995 |
| WO | WO97/07761 A | 3/1997 |
| WO | WO 01/39707 A | 6/2001 |

* cited by examiner

*Primary Examiner*—N. Edwards
(74) *Attorney, Agent, or Firm*—Alston & Bird LLP

(57) ABSTRACT

The present invention relates to a multilayer product 1 having at least one first layer 2, an absorbent intermediate layer 3 and a second layer 4, whereby at least the first layer 2 contains at least one first material 5 and one second material 6. The first layer 2 and/or the second layer 4 is at least partially liquid permeable. The first material 5 has a higher melting point than the second material 6, with the second material 6 creating a bond to the second layer 4.

16 Claims, 5 Drawing Sheets

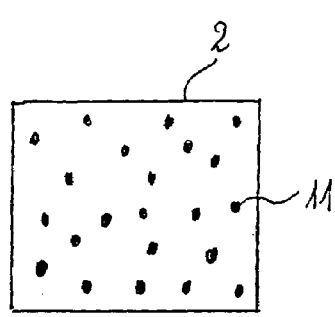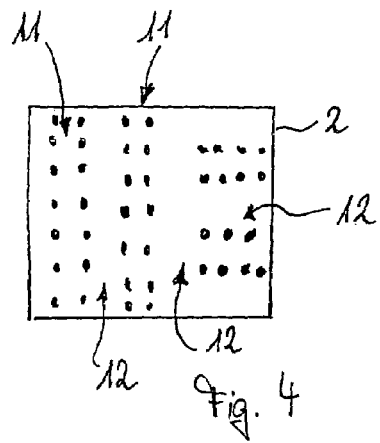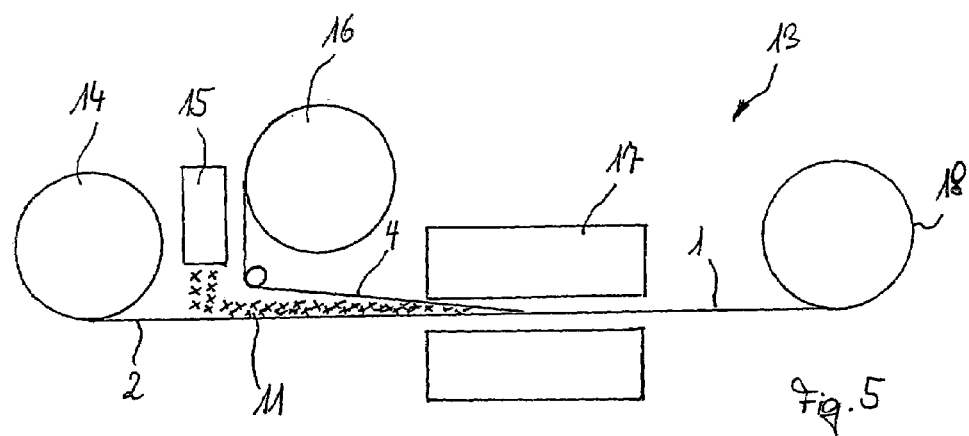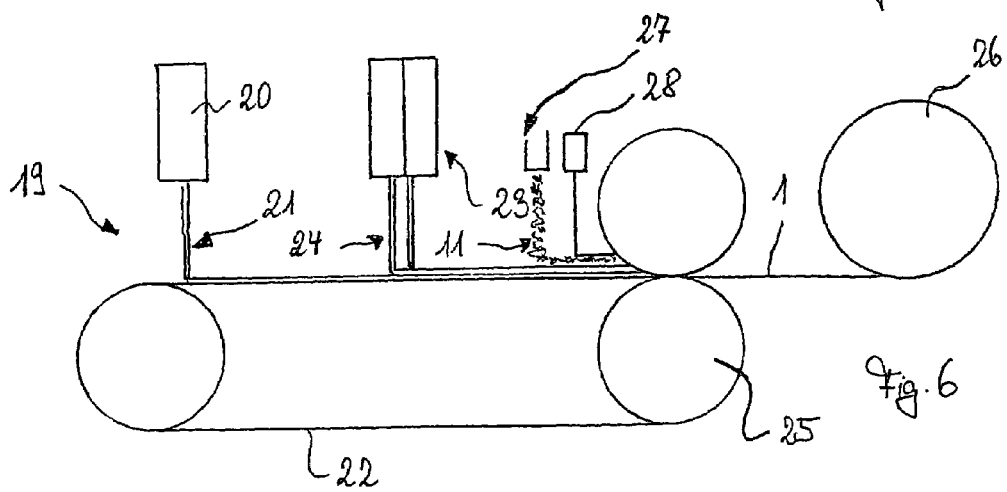

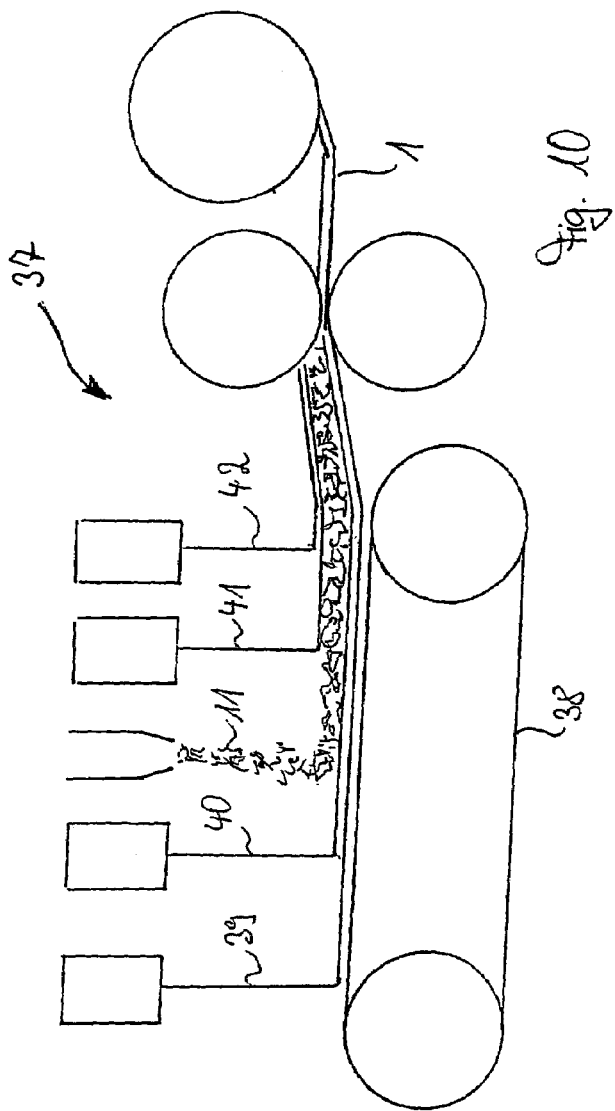
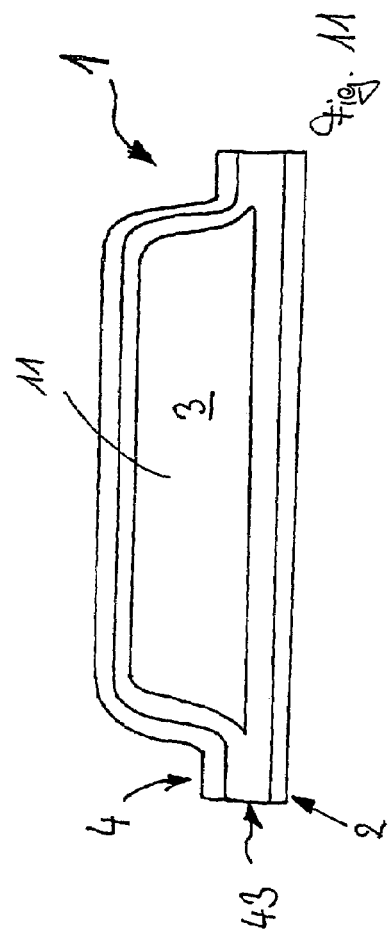

COMPOSITE WITH AN ABSORBENT LAYER

CROSS-REFERENCE TO RELATED APPLICATION

This application is a 35 U.S.C. 371 National phase application of PCT International Application No. PCT/EP03/00635 filed Jan. 23, 2003, which claims priority from German application DE 2002010205828 filed Feb. 13, 2002, the priority of which applications are claimed.

FIELD AND BACKGROUND OF THE INVENTION

The present invention relates to a multilayer product comprising at least one first layer, an absorbent intermediate layer and a second layer. The first layer contains at least one first material and one second material, whereby the first and/or second layer is at least partially liquid-permeable.

World International Patent 95/03019 describes the production of a multilayer product, whereby an absorbent material is arranged between a top layer and a bottom layer. The absorbent material is applied as strips, with an adhesive being applied between the strips in the machine direction. The adhesive causes the top layer and the bottom layer to be bonded together. Therefore, the absorbent material is to be sealed at the sides. European Patent 0 846 455 A1 also describes the production of a multilayer product. In this case again, lateral strips of adhesive are applied to the substrate to subsequently bond a top layer to it. In addition to sealing in the machine direction, sealing in the transverse direction is achieved by supplying an additional top layer and bottom layer to the three-layer product. The additional sealing is achieved by applying a thermoplastic material and then heating until at least reaching the softening point. In this way, the absorbent material is more or less baked to the adjacent top layer and bottom layer. It is known from WO 97/07761 to use a nonwoven material which should enclose an absorbent layer. This nonwoven should be especially dense in comparison with the absorbent material because of its properties. WO 01/39707 also describes the production of a multilayer product which has an absorbent material between a top layer and a bottom layer. The top layer is liquid-permeable and should be a nonwoven, a film, a composite material or the like. The bottom layer should preferably have a spunbonded nonwoven and a meltblown nonwoven. Due to the design of the bottom layer, this should achieve the result that losses of absorbent material in a subsequent further processing of a multilayer product are minor.

SUMMARY OF THE INVENTION

The object of the present invention is to create a multilayer product, which will further prevent loss of material arranged between the layers.

This is achieved with a multilayer product having the features of claim 1 as well as with a method having the features of claim 15. Other advantageous embodiments are characterized in the respective dependent claims.

A multilayer product having at least one first layer, an active intermediate layer, preferably absorbent, and a second layer, whereby at least the first layer has at least one first material and one second material, and the first layer and/or the second layer is at least partially liquid-permeable, has a higher melting point for the first material than for the second material. The second material creates a bond with the second layer. The second material serves in particular to permit a seal between the first layer and the second layer. This preferably makes it possible to omit an additional adhesive. The melting point of the second material is preferably so far from the melting point of the first material that reaching the softening point of the second material does not result in the first material losing its shape and/or softening itself. The softening temperatures of the two materials are preferably separated by a difference of at least 5° C., preferably at least 10° C. It has proven advantageous if the softening point of the second material is in a range of between 10° C. and 15° C., preferably 20° C. from the softening point of the first material. For example, if polyethylene, which has a softening point of approximately 120° C. to approximately 130° C., and polypropylene, which has a softening point of approximately 160° C. to approximately 170° C., are processed together, their softening temperatures can be adapted accordingly through appropriate addition of suitable additives to increase or reduce the softening temperature accordingly. When using the property of softening of the second material, a surface property of same which permits bonding between the first layer and the second layer for the first time is preferably utilized. On reaching the softening temperature, according to one embodiment, the second material should become tacky and in particular should be readily deformable.

According to another embodiment, the second material should have a melting point which has a temperature difference of at least 3° C., preferably at least 8° C., from the melting point of the first material. According to a refinement, the melting point of the second material is such that the softening point of the first material is beneath it.

According to one embodiment, the first layer has first fibers which contain the first material and second fibers which contain the second material. This makes it possible first to use a fiber composite to produce the first layer. Secondly, heating the first layer allows the fiber structure of the second material to be preserved, while the fiber structure of the second material is used for sealing and bonding the first layer to the second layer. In particular, the use of fibers makes it possible to achieve a completely tight fusion between the first layer and the second layer due to the juxtaposition thereof and softening and in particular at least partial melting of the fibers. As a result of this fusion of the two layers, an absorbent material can no longer escape through this bonding site.

According to another embodiment, the multilayer product has a first layer with first fibers, which contain the first material as well as second fibers containing the first material and the second material. The second fibers are preferably bicomponent fibers, whereby the first material is preferably arranged in a core while the second material is runs as a sheath around this core. Another possibility is for fiber sections of the bicomponent fiber to each have a different material.

According to another embodiment, the second material is in contact with the intermediate layer. This advantageously results in the intermediate layer also adhering to the second material in the contact area, if this area is heated accordingly. This leads to immobilization of the absorbent material of the intermediate layer. In addition, this also achieves the result that the absorbent material in this area itself forms a barrier through which it is extremely difficult for the absorbent material above it to penetrate.

For example, an absorbent fiber and/or an absorbent powder is used for the absorbent intermediate layer. There is also the possibility of using a gel, granules or the like. In addition, there is also the possibility of using mixtures of material. The absorbent intermediate layer may also be provided with an additional material having other functions than that of absorption. For example, the additional material may result in a special strength, stiffness or the like.

According to another embodiment, the second material has a non-positive connection with the second layer. A non-positive connection in this sense means, for example, that the second material is chemically and/or physically bonded to the second layer and/or penetrates into the second layer, if not actually permeating through it. After solidification of the second material, this ensures that the bond thus created can be severed only by applying a force. According to another embodiment, the second material seals the intermediate layer at the sides in cooperation with the second layer. The second material preferably seals the intermediate layer all the way around.

Preferably only the second material of the first layer is in contact with the second layer. This makes it possible, for example, for the first material of the first layer to have a special task or a special function. For example, it may be designed to be especially hydrophilic, while the second material is less hydrophilic. If a liquid bridge is created between the first layer and the absorbent material, the latter absorbs the liquid, with the second layer ensuring, because of the lower hydrophilic property, that there will be an interruption in the suction flow thus created. On the other hand, a greater hydrophilic property of the second material in comparison with that of the first material can ensure that there will be an increased capacity to absorb liquid to the absorbent material of the intermediate layer by means of the gradient thus formed.

It has also proven advantageous if the multilayer product is designed so that the second layer also contains the second material of the first layer. This permits an especially tight bond between the first layer and the second layer, in that preferably both materials are heated to approximately same temperature and preferably are at least softened. In particular, both materials can be heated to the extent that they flow into one another and thus yield a type of welding. This is especially advantageous inasmuch as it yields high strength values especially with respect to transverse forces and tensile forces. According to another embodiment, the multilayer product has a first layer, which contains essentially a high-melting polymer, e.g., a polypropylene, as the first material and a low-melting polymer, e.g., polyethylene, as the second material. The polyethylene has, for example, a melting point between 106° C. and 155° C., while the polypropylene has a higher melting point.

One area of application of the multilayer product is to use it in a hygiene article to absorb a fluid. In addition, the multilayer product may also be used in household applications or other areas where a liquid or some other fluid is to be absorbed. In particular, the multilayer product can be used to influence an odor in the environment. For example, odors that are perceived as unpleasant can be absorbed and stored by the product, e.g., by binding them or otherwise neutralizing them.

According to another example of this invention, a method of producing a multilayer product having at least one first layer, an absorbent intermediate layer and a second layer is created. At least the first layer has at least one first material and one second material, the first layer and/or the second layer being at least partially liquid-permeable. A first material which has a higher melting point than the second material is used, whereby the second material is heated at least approximately up to its melting point, and the first layer and the second layer are bonded together by means of the heated second material.

According to another embodiment, a powder is applied to the second material to form the absorbent intermediate layer at least in part before the second material is heated, whereby the powder is at least partially bonded to the second material. In particular, the second material is heated until the intermediate layer is sealed at the sides.

According to another embodiment, the multilayer product is punched out of a sheeting which is supplied continuously. The contours of the multilayer product are preferably arranged so they are offset from one another on the sheeting thus supplied, so that waste of sheeting material left over is minimal.

Examples of embodiments of this invention are given below, their features being combinable with one another to form advantageous refinements.

The multilayer product is used, for example, to introduce a powder, e.g., SAP, into cellulose (fluff) preferably for hygiene applications, in particular as absorbent layers for diapers, to keep one or more active powders, e.g., in a three-dimensional fiber structure, in place in the multilayer product, to secure a mixture of fibers and powder and/or another absorbent material in a desired geometric shape and/or to hold SAP fibers, for example, in and/or between airlaid materials or nonwovens. For example, a hot adhesive powder, e.g., PE or EVA powder or fibers may be used in addition as a fixation aid, leading to bonding of surrounding fibers and/or grains of powders because of the heating of the multilayer product.

An example of a multilayer product is described in greater detail below. The product has a first outer layer. The first outer layer may include thermoplastic fiber layers, a film and/or a nonwoven. They preferably have a first component or a first layer of a homopolymer which has a higher melting point, e.g., polypropylene. This has the advantage that it yields a good processing property, especially with respect to processing under the influence of heat, where a high strength is retained. In particular, this prevents sticking to guide rollers or the like. A second component and/or a second layer has in part a low melting point in comparison with the first layer and/or component. For example, a bicomponent fiber is used. The bicomponent fiber is preferably designed as a side-by-side structure or as a core-sheath structure, in particular made of a mixture of material containing polypropylene and/or polyethylene. According to another embodiment, the second component and/or the second layer has a low melting part, e.g., a polyethylene. This is used to achieve a rapid melting under the influence of heat, and thus to achieve adhesion to the powder. The part, such as a polypropylene, which does not melt until reaching high temperatures then ensures a tight bond of the second layer and/or component with the first layer and/or component. An intermediate layer, preferably containing active particles, is connected to the components. These may be, in particular, SAP, zeolites, activated carbon, odor and liquid absorbers, pH indicators and/or regulators, coloring agents, complexing agents EDTA (ethylenediaminetetraacetate), aroma or flavoring substances. The particles preferably have a certain particle size distribution, so there is no leakage of particles through the corresponding surrounding layers. According to another embodiment, the particle size distribution is designed so that finer particles are preferably surrounded by somewhat larger particles. In particular, the larger particles may form a barrier to prevent the escape of the finer particles toward the outside through the surrounding layers and vice versa. A second outer layer is situated adjacent to the intermediate layer. This second outer layer preferably has the same fiber layer as the first outer layer. In particular a low-melting part of the second outer layer is situated so it faces the powder. However, this part may also be non-self-adhesive.

Additional embodiments of such a principle of a multilayer product may have the following features:

A nonwoven layer may be replaced and/or supplemented by a film and/or a foam material. The materials may be laminated, in particular by producing them by multilayer extrusion;

In particular, an outer layer may be based on cellulose or a similar material. In particular, non-self-adhesive materials may be used, such as those used in airlaid materials, tissue or paper, for example;

The nonwoven that is used may be finished with a hydrophilic or hydrophobic, oleophilic or oleophobic finish, e.g., by using the respective additive package or by application of substances after production of the nonwoven or fiber. The nonwoven may be transparent or it may be designed with a color by pigmentation. The type of nonwoven may be varied. For example, staple fibers, spunbonded nonwovens, meltblown nonwovens or other fiber or nonwoven materials may be used;

In addition to the polyolefins polypropylene and polyethylene and mixtures thereof which are preferred for use, other thermoplastic polymers may also be used, in particular polyesters, polyamides [nylons], derivatives thereof, as copolymers or block copolymers. In particular, it has proven advantageous if bicomponent fibers or multicomponent fibers, which have the corresponding desired properties or sealing capability of layers, are used;

The material used in the intermediate layer, in particular a powder, may be applied over the entire area or only over a portion of the area. In addition, there is the possibility of providing this material in a profiled form over a cross section in the longitudinal direction, the transverse direction or in the vertical direction. This depends in particular on the application of the subsequent finished product. For example, for hygiene products, the intermediate layer may be arranged in such a way that the desired body contours and probable contact surfaces of fluids are adapted accordingly.

To support a bonding of the first layer and the second layer and/or one of the two layers with a material of the intermediate layer, an additional adhesive, in particular a hot-melt adhesive, may be applied over all or part of the surface. The first layer and the second layer are preferably supplied as roll goods by means of unwinding. The intermediate layer is arranged in particular as a freely portionable material layer between the first layer and the second layer according to predefinable geometries. In addition, there is also the possibility of providing inline production. For example, a nonwoven and/or film production installation is provided, with a corresponding feed for the material of the intermediate layer and/or the second layer being provided downstream from this installation, with a subsequent material bonding station. Other advantageous embodiments and refinements are illustrated in the drawings which follow. The features illustrated there can be combined with the refinement mentioned above but not described in greater detail here.

BRIEF DESCRIPTION OF THE DRAWINGS

These figures show:

FIG. 3 a first view of a first layer;

FIG. 4 a second view of a first layer;

FIG. 5 a first device for producing a multilayer product;

FIG. 6 a second device for producing a multilayer product;

FIG. 10 a third device for producing a multilayer product, and

FIG. 11 a cross section through a multilayer product.

DETAILED DESCRIPTION

Figure 1:
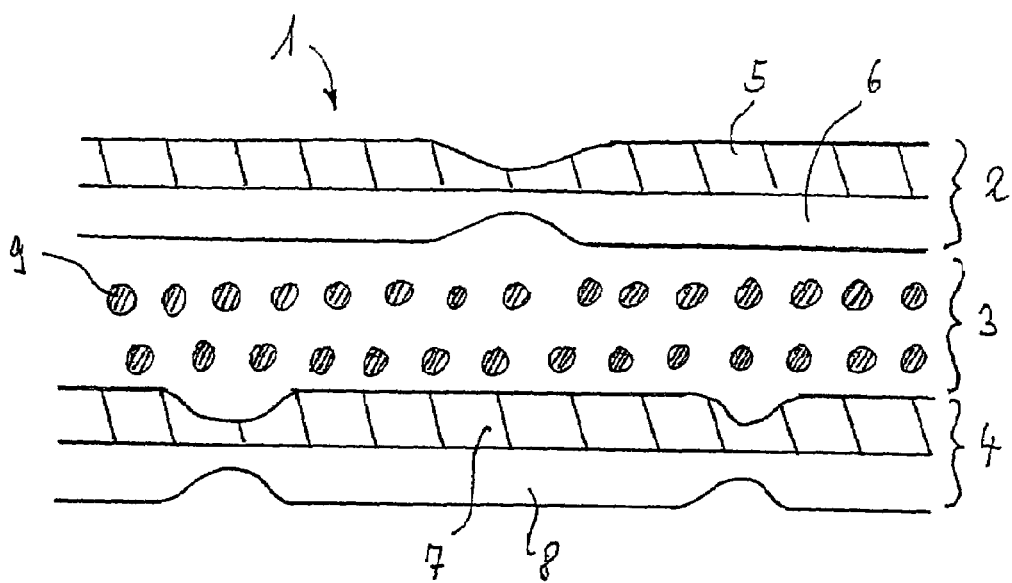
FIG. 1 a multilayer product with a first layer, an absorbent intermediate layer and a second layer.

FIG. 1 shows a first multilayer product 1 with a first layer 2, an absorbent intermediate layer 3 and a second layer 4. The first layer 2 has a first material 5 and a second material 6. The second layer 4 has a third material 7 and a fourth material 8. The first layer 2 and the second layer 4 are both preferably nonwoven materials. At least one of the two materials 2, 4 may also contain a film and/or a foam. The first material 5 of the first layer 2 contains, for example, a polypropylene. It is preferably produced as a spunbonded nonwoven. The second material 6 is polyethylene, for example. The third material 7 in turn preferably also contains polyethylene, but the fourth material 8 preferably contains polypropylene. The absorbent intermediate layer 3, which contains particles 9, for example, according to this embodiment, is arranged between the first layer 2 and the second layer 4. The particles are preferably held in place in the intermediate layer 3 at least partially by the polyethylene, which is softened by an increase in temperature. In addition, the polyethylene is heated to the extent that the additional material 6 of the first layer 2 is sealed to the third material 7 of the second layer 4 and then escape of the particles through this seal is prevented. In addition to particles 9, superabsorbent fibers, mixtures of superabsorbent fibers and particles, water-soluble fibers, in particular in a mixture with particles and/or powder, e.g., of polyvinyl alcohol, e.g., cellulose or viscose and/or other certain liquid-absorbing materials may also be arranged in the intermediate layer 3. In addition, cosmetics, dyestuff, blood coagulants, blood anticoagulants, citric acid and/or electric conductors, either individually or in a mixture of the materials mentioned above, may be present in the intermediate layer 3.

Figure 2:
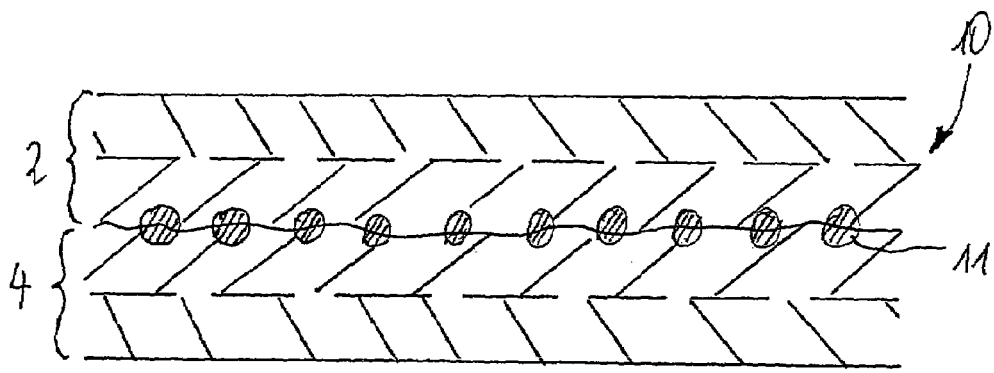
FIG. 2 a second multilayer product.

FIG. 2 shows a second multilayer product 10 in a cross-sectional view. The multilayer product 10 has a first layer 2 and a second layer 4. The first layer 2 and the second layer 4 have a bicomponent fiber spunbonded nonwoven facing inward, preferably containing polypropylene and polyethylene. The arrangement of polypropylene and polyethylene is preferably a side-by-side arrangement. The multilayer product 10 is heated after stacking the layers. Due to this heating, the material which has a lower melting point is made to soften more rapidly. In particular, the heating temperature may result in the material having the lower melting point at least beginning to melt, while the other material is still completely in its solid form. An intermediate layer material 11, which is arranged between the first layer 2 and the second layer 4 is accommodated by the partially melted material and is embedded in it. According to another embodiment, instead of heating the entire product, only the intermediate layer may be heated in particular. Especially if the intermediate layer consists of particles or fibers, which are essentially less dependent on temperature than the surrounding layers, such a procedure allows savings on energy costs. The intermediate layer material is brought to a suitable temperature, e.g., by a corresponding heating, e.g., infrared, hot air, heated rollers or inductive heating as well as steam heating, so that the intermediate material is bonded to the layers surrounding it. The intermediate material is heated, for example, when applying it to the first or second layer by a suitable applicator device according to a desired application and a desired application geometry.

FIG. 3 shows a first view of an intermediate layer material 11 which is applied to a first layer 2. As indicated schematically, the intermediate layer material 11 is applied over the entire area. The application itself is preferably performed in such a way that it is done without any additional cellulose. The intermediate layer material 11 is covered by a second layer 4 in a working step which is not shown here, and it is sealed at the sides because of the properties of the first layer 2 and the second layer 4.

FIG. 4 shows another first layer 2 on which the intermediate layer material 11 is arranged. The arrangement of the intermediate layer material 11 follows a defined application geometry. For example, free zones 12 may be arranged between application areas of intermediate layer material 11. The free zones 12 may be arranged in the machine direction (MD) and in the transverse or crosswise direction (CD). If the material is then passed through a calender after application of a second layer, the free zones 12 may later form sealing zones, by means of which the first layer 2 is bonded to an opposite second layer. Then the layers may be cut through this sealing zone, to obtain individual absorbent pads in this way.

FIG. 5 shows a first device 13 for producing a multilayer product 1. The first layer 2 is supplied from a first drum 14 to an application station 15 for the intermediate layer material 11. The second layer 4 is applied to the intermediate layer material 11 from a second drum 16. In the downstream heating station 17, the multilayer product 1 is heated. This causes the second material (not shown in greater detail here) of the first layer 2 to be heated to the extent that it reaches at least its softening temperature and is bonded to the opposite second layer 4. In addition, heating the second material also yields the result that the intermediate layer material 11 is fixed in position by the second material. Bonding of the first layer 2 to the second layer 4 and/or bonding of the intermediate layer material 11 to at least the first layer 2 can thus be supported by applying a pressure to the layers. The pressure can be exerted upstream from the heating station 17 and/or downstream from the heating station 17 as well as during the heating. The heating station 17 may apply the required heat flow to the multilayer product over the full-area or only part of the area. The heat flow may be introduced into the multilayer product by infrared heating, hot air, steam, for example, by heated rollers, by inductive heating or other measures. In addition, there is the possibility that the intermediate layer material 11 from the application station 15 may be applied in a heated condition to the first layer 2, where the material having the low melting point softens accordingly and sinks into it there. In addition, the bonding of the first layer 2 to the second layer 4 may also be accomplished subsequently through the heating station 17. With this first device 13, a windup station 18 is situated downstream from the heating station 17. A cutting device (not shown here) may also be provided to divide the layers into sections, preferably in the machine direction and/or in the transverse direction.

FIG. 6 shows in a schematic diagram a second device 19 for producing a multilayer product 1. The second device 19 is an inline device. A first spunbonded nonwoven 21 is deposited from a first spunbonded nonwoven bank 20 onto a revolving belt 22. From a second spunbonded nonwoven bank 23, a material which at least partially has a different melting point than that of the first spunbonded nonwoven 21 is applied to this first spunbonded nonwoven 21, which is not yet solidified. Preferably a second spunbonded nonwoven 24 is applied. This second spunbonded nonwoven 24 is in particular a bicomponent fiber material, preferably made of polypropylene and polyethylene. The polypropylene and polyethylene may be distributed in a fiber in a variety of ways. For example, there is the possibility of providing a side-by-side arrangement. A core-sheath arrangement is also possible. Another arrangement provides for the polypropylene and polyethylene to be arranged in segments at the surface and/or shortly in front of the surface of the fiber. The first spunbonded nonwoven 21 and the second spunbonded nonwoven 24 are then calendered by means of a thermobonding calender 25. Downstream from the thermobonding calender 25 is a second windup station 26. A second application station 27 and a third spunbonded nonwoven bank 28 may be arranged between the second spunbonded nonwoven bank 23 and the thermobonding calender 25. The thermobonding calender 25 in particular is designed so that the layers are not only embossed and compressed, but instead the multilayer product 1 is preferably also created with sealing surfaces between the top and bottom layers. For example, the calender may have corresponding elevations and/or recesses which have been provided around the circumference of one of the embossing calender rolls. Preferably a cutting unit (not shown in detail here) is also arranged between the second windup station 26 and the thermobonding calender 25, performing a separation cut, executed in the machine direction in particular, between adjacent sealed areas. To do so, for example, the intermediate layer material 11 coming from the second application station 27 and inserted into the intermediate layer between a top layer and a bottom layer is applied according to a predefined pattern. In addition to the use of a spunbonded nonwoven, there is also the possibility of providing a staple fiber nonwoven and/or film, foam and/or meltblown nonwoven.

Figure 7A:
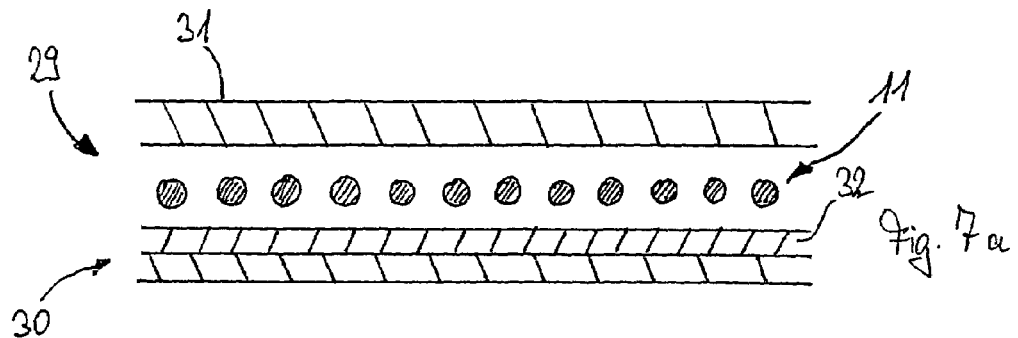
FIG. 7*a* a multilayer product that is not yet sealed.
Figure 7B:
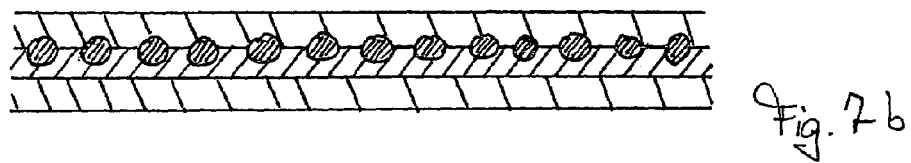
FIG. 7*b* the product shown in FIG. 7*a* in a sealed form.

FIG. 7a shows a multilayer material 29 that has not yet been sealed, and FIG. 7b shows the multilayer material 29 after it has been sealed. The multilayer material 29 has a first outer layer 30 which is composed of two layers. The second outer layer 31 is a single layer. The intermediate layer material 11 is arranged between the first outer layer 30 an the second outer layer 31. According to the schematic diagram, the intermediate layer material 11 consists of functional particles. The particles are absorbent in particular. However, they may also have other functions, e.g., releasing a scent. In addition, they may also be activatable by certain influences. These influences may be, for example, heat, moisture, electric current, pressure or a pulse. The particles then enter a thermally activatable component 32 of the first outer layer 30. As shown in FIG. 7b, they are held together in this way. Through an appropriate application of pressure, the intermediate layer material 11 may also at least partially enter the surface of the second outer layer 31.

According to another embodiment not shown here, instead of the particles illustrated in FIGS. 7a and 7b, fibers may also be used. Preferably fibers as well as particles are active. Active means in particular that they are equipped with a special function. Another embodiment which is independent of the former provides for a layer to be provided with an active coating and/or for activatable components to be present in this coating. After drying and/or cross-linking with the layer, the coating may not be as elastic and/or flexible as the layer itself. By applying a layer arranged above it and then sealing, this prevents the coating or components thereof from being able to pass through the layers or the seal if the coating is damaged or flakes off. For example, such a coating may be a superabsorbent coating.

Figure 8:
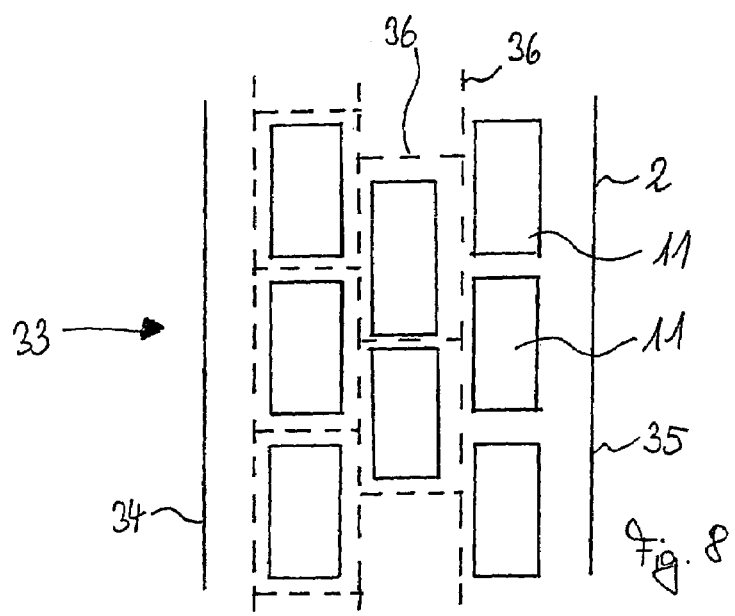
FIG. 8 a first arrangement of intermediate layers on a first layer.

FIG. 8 shows a first arrangement 33 of intermediate layers on a first layer 2. The intermediate layer materials 11 are arranged between a first edge 34 and a second edge 35. These materials may be particles and/or fibers. The goal is to utilize a production width of the first layer 2. To do so, the intermediate layer materials 11 may be deposited in strips which are continuous or, as shown, they may be deposited as subdivided geometric shapes. In addition, there may also be subsequent cutting planes 36 which are offset relative to one another. However, the cutting planes may also be aligned relative to one another so as to yield parallel cutting planes that are continuous in the machine direction. Cutting planes that are also parallel but are offset relative to one another may also be provided in the transverse direction. The cutting planes are indicated with dotted lines as an example.

Figure 9:
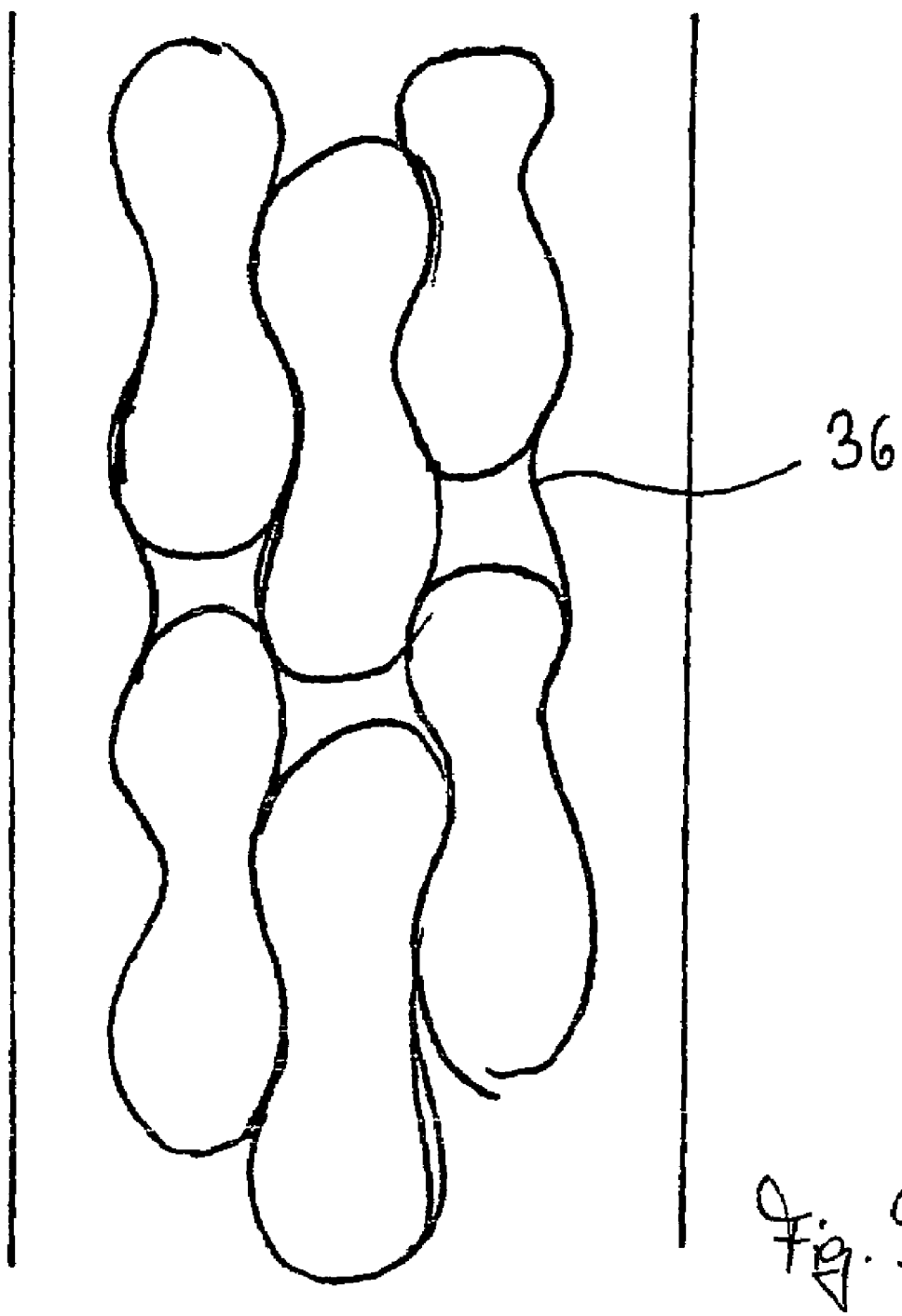
FIG. 9 a second arrangement of intermediate layers on a first layer.

FIG. 9 shows another arrangement of cutting planes 36. In this case, the cutting planes do not run along a straight line but instead run along a curvature or they are at least partially round. For example, such cutting planes 36 may be achieved by the fact that the first layer 2 and/or the multilayer product 1 formed from them is passed through a punch. In addition, it is also possible for such a cutting plane to be produced by a suitably designed calender. The calender has a roll, which has a suitably shaped surface geometry.

FIG. 10 shows a third device 37 for producing a multilayer product 1. A spunbonded nonwoven 39, preferably consisting of polypropylene and/or a copolymer, is deposited on a second revolving belt 38. A bicomponent fiber spunbonded nonwoven 40 of polypropylene and polyethylene is deposited on the spunbonded nonwoven 39. Then a powder-fiber mixture is applied, forming a subsequent intermediate layer of the multilayer product 1. This is in turn followed by application of a second bicomponent fiber spunbonded nonwoven 41 and a subsequent additional spunbonded nonwoven 42. This multilayer material is then calendered, sealed and rolled up for further processing.

FIG. 11 shows a schematic diagram of a cross section of a multilayer product 1. The multilayer product 1 has a seal 43 between the first layer 2 and the second layer 4. The seal 43 is formed, for example, by heating the bicomponent fiber spunbonded nonwoven produced in FIG. 10 in the subsequent calendering to the extent that the materials are fused together and penetrate into one another mutually. This leads to a mutual sealing which prevents the intermediate layer material 11 from escaping out of the absorbent intermediate layer 3.

The invention claimed is:

1. A composite multilayer absorbent product comprising: a liquid permeable spunbond nonwoven first layer, a second layer, and an adsorbent intermediate layer located between said first and second layers, said absorbent intermediate layer including a blend of absorbent fibers and a powder, said blend being located in selected areas across the multilayer absorbent product and defining zones between said selected areas that are free of said blend, at least the first layer including a first polymeric material and a second polymeric material, wherein the first polymeric material has a higher melting temperature than the second polymeric material, and wherein the second polymeric material of the first layer creates a bond with the second layer in said zones, and the powder of the intermediate layer is immobilized by the second polymeric material in said selected areas.

2. The multilayer product according to claim 1, wherein the first layer contains first fibers comprising the first material and contains second fibers comprising the second material.

3. The multilayer product according to claim 1, wherein the first layer contains first fibers comprising the first material and contains second fibers comprising the first material and the second material.

4. The multilayer product according to claim 1, wherein the second material is in contact with the intermediate layer.

5. The multilayer product according to claim 1, wherein the second material is chemically and/or physically bonded to the second layer and/or penetrates into the second layer.

6. The multilayer product according to claim 1, wherein the second material seals the intermediate layer at the sides in interaction with the second layer.

7. The multilayer product according to claim 1, wherein only the second material of the first layer is in contact with the second layer.

8. The multilayer product according to claim 1, wherein the second layer contains the second material of the first layer.

9. The multilayer product according to claim 1, wherein the second material of the first layer is at least partially fused with the second layer.

10. The multilayer product according to claim 1, wherein the first layer comprises a homopolymer as the first material and contains a polyethylene as the second material.

11. The multilayer product according to claim 1, wherein the first layer comprises bicomponent fibers.

12. The multilayer product according to claim 1, wherein a hygiene article contains the multilayer absorbent product to absorb a fluid.

13. The multilayer product according to claim 1, wherein an article contains the multilayer absorbent product to influence the odor of its environment.

14. The multilayer product according to claim 11, wherein the bicomponent fibers contain said first and second materials.

15. A composite multilayer absorbent product comprising a liquid permeable spunbond nonwoven first layer, a second layer, and an absorbent intermediate layer located between said first and second layers, said absorbent intermediate layer including a blend of absorbent fibers and a powder, said blend being located in selected areas across the multilayer absorbent product and defining zones between said selected areas that are free of said blend, at least the first layer including bicomponent fibers containing a first polymeric material and a second polymeric material, wherein the first polymeric material has a higher melting temperature than the second polymeric material, and wherein the second polymeric material of the bicomponent fibers of the first layer creates a bond with the second layer in said zones, and the powder of the intermediate layer is immobilized by the second polymeric material in said selected areas.

16. The multilayer product according to claim 15, wherein the first polymeric material comprises polypropylene and the second polymeric material comprises polyethylene, and wherein the polymeric materials are in a side-by-side arrangement in the bicomponent fibers.

* * * * *